United States Patent
Boese et al.

(10) Patent No.: US 7,778,689 B2
(45) Date of Patent: Aug. 17, 2010

(54) METHOD FOR LOCALIZING A MEDICAL INSTRUMENT INTRODUCED INTO THE BODY OF AN EXAMINATION OBJECT

(75) Inventors: Jan Boese, Eckental (DE); Bernhard Sandkamp, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 721 days.

(21) Appl. No.: 11/524,665

(22) Filed: Sep. 21, 2006

(65) Prior Publication Data
US 2007/0066889 A1 Mar. 22, 2007

(30) Foreign Application Priority Data
Sep. 21, 2005 (DE) .................. 10 2005 045 093

(51) Int. Cl.
*A61B 5/05* (2006.01)
*A61B 5/04* (2006.01)
*A61B 19/00* (2006.01)

(52) U.S. Cl. .............. 600/424; 600/547; 600/373; 600/382; 128/899

(58) Field of Classification Search .......... None
See application file for complete search history.

(56) References Cited

U.S. PATENT DOCUMENTS

| | | | |
|---|---|---|---|
| 5,697,377 A | 12/1997 | Wittkampf | |
| 5,944,022 A | 8/1999 | Nardella et al. | |
| 6,298,261 B1 | 10/2001 | Rex | |
| 6,594,521 B2 | 7/2003 | Tucker | |
| 6,678,552 B2 | 1/2004 | Pearlman | |
| 7,440,796 B2 * | 10/2008 | Woo et al. | 600/547 |
| 2003/0216630 A1 * | 11/2003 | Jersey-Willuhn et al. | 600/407 |
| 2004/0201380 A1 * | 10/2004 | Zimmermann et al. | 324/334 |
| 2005/0054911 A1 * | 3/2005 | Nachman et al. | 600/411 |
| 2006/0085049 A1 * | 4/2006 | Cory et al. | 607/48 |

FOREIGN PATENT DOCUMENTS

DE  43 06 037 A1  9/1994

* cited by examiner

*Primary Examiner*—Long V Le
*Assistant Examiner*—Angela M Hoffa

(57) ABSTRACT

A method for localizing a medical instrument introduced into the body of a patient, comprising:
arranging at least four electrodes on the body of the patient,
recording three-dimensional image data of a region of the patient,
determining a conductivity model of the patient via the image data,
determining electric field distribution when a voltage or current is applied for at least three electrode pairs formed from the four electrodes via the conductivity model and spatial positions of the electrodes, not all the electrodes lying in one plane,
applying a voltage or a current at each electrode pair and determining three voltage values at an electrode of the medical instrument for the three electrode pairs, and
determining the spatial position of the medical instrument as the intersection of equipotential surfaces assigned to the three voltage values at the electrode of the medical instrument.

17 Claims, 3 Drawing Sheets

METHOD FOR LOCALIZING A MEDICAL INSTRUMENT INTRODUCED INTO THE BODY OF AN EXAMINATION OBJECT

CROSS REFERENCE TO RELATED APPLICATIONS

This application claims priority of German application No. 10 2005 045 093.8 filed Sep. 21, 2005, which is incorporated by reference herein in its entirety.

FIELD OF THE INVENTION

The invention relates to a method for localizing a medical instrument, in particular a catheter or guide wire, introduced into the body of an examination object.

BACKGROUND OF THE INVENTION

Minimally invasive interventions in the human body or even in animals are carried out as interventional methods with the aid of medical instruments such as for example catheters or guide wires. The area in which the introduced catheter and/or the introduced guide wire is/are located cannot be viewed directly by the person who is carrying out the examination. Determination of the current spatial position of the medical instrument is, however, necessary in order to convey the instrument optionally to the correct location for a treatment or to obtain information about a defined area in the body of the examination object. The medical instrument is therefore as a rule localized by means of an X-ray system, for example by fluoroscopy or angiography.

However, a problem with localization by means of an X-ray system is that as a rule no three-dimensional information can be obtained about the position of the catheter, only projection images without depth information. Furthermore, the patient is often exposed to a considerable X-ray dose.

The localization of catheters is of particular importance in interventional methods in the electrophysiological field. For example, cardiac arrhythmias are treated with the aid of electrophysiological interventions, whereby areas of defective cardiac conduction are obliterated in a targeted manner. To achieve this, medical instruments such as catheters have to be navigated in the three-dimensional cavities of the heart, while on the other hand the interventions are often prolonged and in the case of X-ray localization the long duration means that high radiation doses have to be applied.

In order to avoid disadvantages of this type, other non-X-ray-based localization methods have been proposed which have become established in particular in the aforementioned field of electrophysiology. Examples which can be cited include systems which are based on electromagnetic locating and are structured similarly to the global positioning system or the like. Besides these, there are proposals to locate medical instruments for use in electrophysiology via a simple measurement of the resistance of the body of the examination object. In each case, two electrodes on mutually perpendicular axes are stuck to the skin of the patient. A known voltage is applied between the two electrodes, the voltage then being measured at an electrode of the medical instrument. It is assumed that inside the patient the voltage drops in a linear manner so that from three voltages for three perpendicular electrode axes, which voltages are measured in succession on the medical instrument, the three spatial coordinates of the catheter can be inferred. Such a method is described in U.S. Pat. No. 5,697,377. In contrast to methods which are based on electromagnetic locating, no special and thus expensive catheters are required for this. A proportionality constant between voltage and spatial distance is determined for the locating by a calibrating method.

In the method of measuring the resistance of the body, there is, however, the problem that in reality the voltage drop does not take place in a linear manner but depends on the individual geometry and conductivity distribution in the body. Localization which is achieved through measurement of the resistance of the body as outlined above is therefore not exact with deviations in the heart, for example, of several millimeters, which can give rise to problems for examinations or treatments. In addition, a total of at least six additional electrodes have to be stuck onto the patient, which increases the time expended on conducting the examination.

SUMMARY OF THE INVENTION

The object of the invention is therefore to indicate an in this regard improved method for localizing a medical instrument, in particular a catheter or guide wire, introduced into the body of an examination object.

To achieve this object, a method of the above type is provided which comprises the following steps:

arrangement of at least four electrodes on the body of the examination object, recording of three-dimensional image data of a body region of the examination object that is of interest by means of an imaging medical examination device, determination of a model of the electrical conductivity of the examination object as a function of the recorded three-dimensional image data, determination of the electric field distributions when a voltage and/or current is/are applied for at least three different electrode pairs formed from the four electrodes as a function of the conductivity model and of the spatial positions of the electrodes, not all the electrodes lying in one plane, determination of a voltage value at an electrode of the medical instrument when a voltage and/or current is/are applied to each electrode pair for the at least three electrode pairs and application of a voltage and/or a constant current to each electrode pair and determination of a voltage value at an electrode of the medical instrument for the at least three electrode pairs and determination of the spatial position of the medical instrument as the point of intersection of the equipotential surfaces assigned to the at least three voltage values at the electrode of the medical instrument.

According to the invention, the medical instruments such as, for example, a catheter is thus localized on the basis of an impedance measurement, for which four electrodes are firstly arranged on the body of the examination object. It is, of course, possible to place more than four electrodes for example on the skin to the examination object. In contrast to known methods, an arrangement of the electrodes in orthogonal pairs is not required. Depending on the type of examination, electrodes can optionally be used which are in any case provided for data-recording or for monitoring, for example in electrophysiological procedures. The extracardial electrodes which are required in any case and which for this purpose are connected, as is an electrode of the medical instrument, to a system for generating and detecting signals, can advantageously be used here.

A three-dimensional image recording of the body region of interest, i.e. of a sub-area or of the whole body of the examination object, is then produced. This can, for example, be a recording using the technique of rotational angiography, which recording is carried out in a catheter laboratory and in which, due to modern techniques, the radiation loading for the patient is low. The term "rotational angiography" is used hereinbelow by way of example for 3D-imaging methods which can be implemented during an intervention. Where cardiac recordings are to be produced, then a gating controlled by an electrocardiogram is advantageously used so that the heart can be mapped without motion artifacts.

A model of the electrical conductivity of the examination object is determined as a function of the three-dimensional image data recorded in this way. The determination of a conductivity model from magnetic resonance images in conjunction with voltages or currents being applied on the surface of a body is described for example in U.S. Pat. No. 6,594,521 B2. Such a conductivity model can for example be constructed from individual shells or finite elements.

The electrical field distributions are then determined as a function of the conductivity model and the spatial positions of the electrodes. For each of the at least three electrode pairs formed from two electrodes, equipotential surfaces are determined which indicate the locations of a constant voltage if a defined voltage is applied at the electrodes of the pair. For this, the position of the electrodes must be known, the imaging being carried out, for example, as part of a rotational angiography in which the electrodes in the three-dimensional images are localized automatically or manually. The field distribution can be determined from the conductivity model and the electrode positions alone, without voltages actually having to be applied at the electrodes. Nonetheless, it is possible to apply voltages and optionally to conduct measurements in addition. From the at least four electrodes, three pairs are formed such that not all the electrodes lie in a plane, in order to obtain information about all spatial directions.

Voltages are then applied at two electrodes respectively, i.e. an electrode pair. Instead of a voltage, a current can be applied in order to offset fluctuations in resistance, in particular in skin resistance where skin electrodes are applied.

A voltage value at an electrode of the medical instrument, for example at an electrode on a catheter, is determined for the voltage and/or current currently being applied. Determination of this voltage value is carried out for the at least three electrode pairs in which not all the electrodes lie in a plane.

The spatial position of the medical instrument is then determined as the point of intersection of the equipotential surfaces assigned to the at least three voltage values at the electrode of the medical instrument, as a result of which a localization is achieved which, in contrast to the previous methods assume a linear voltage drop, reproduces precisely the overall geometry of the arrangement. Thus, in contrast to these known methods, an accuracy of reproduction is achieved which lies at approximately 1 mm. The equipotential surfaces relating to the voltage values at the medical instrument are known from the determined or computed electrical field distributions. In the case of instruments which possess multiple electrodes, the method is applied for each electrode individually.

The applied voltage or the applied current can be constant. Alternatively, an alternating voltage or an alternating current with a constant mean value determined over a certain time period can also be applied. Voltage and current are thus defined or predetermined.

The model of conductivity can be determined as a function of an assignment of intensity values of the image data to conductivity values. Even a rough conversion of intensity values into conductivity values enables, in comparison with previous methods, a better recording of the geometry and thus a more precise localization of the catheter or of another medical instrument.

To determine the model of conductivity, at least two different tissue types with differing conductivities can be differentiated in the body of the examination object, in particular bone tissue and/or organ tissue and/or air and/or water-equivalent tissue. For example, differentiating between air and water-equivalent tissue is an obvious solution for implementing a computer tomography or in rotational angiography recordings. Depending on the type of area of interest in the body of the patient, a distinction can be made, for example, between the respective organ tissue, for example lung tissue, and other tissue. The conductivity model can be improved arbitrarily by taking into account more than two tissue types. For an estimate of the conductivity model of the patient, data can be used which is available, for example, in medical databases or can be determined with the aid of program means using specific data of the patient.

The three-dimensional image data can be recorded as part of a rotational angiography and/or a computer tomography and/or a magnetic resonance recording and/or an ultrasound recording. Optionally, the electrodes must then already be stuck on and be suitably recognizable when the three-dimensional recording is made. Besides skin electrodes, electrodes inside the body and whose position is known can also be used, for example electrodes of fixed-position catheters or of implants.

For recording the three-dimensional image data and/or determining the spatial position of the electrodes, image data of different image recording methods can be combined. It is thus possible to produce, for example, an ultrasound recording and to combine this with the recordings of a rotational angiography in order in this way to determine sufficiently accurately the position of the electrodes in space. In this way, an automatic localization of the electrodes in the three-dimensional images can be carried out optionally as part of a rotational angiography, it being possible for errors to be avoided by merging these images with ultrasound images in which the electrodes have optionally been made recognizable. The merging of images is particularly advantageous regarding the use of 3D images on which the electrodes are not shown because they had not yet been stuck on at the time of the recording. Such image data can be combined by means of known 3D/3D registration methods with e.g. rotational angiography data, the latter containing the electrode positions. In this way, the electrode positions can be transferred to the first 3D image dataset. Moreover, a better conductivity model can possibly be created through the additional image data of different recording methods.

According to the invention, the spatial position of the electrodes can be determined when the three-dimensional image data is recorded as part of a rotational angiography and/or by being rendered visible for the respective image recording method. Thus, as previously mentioned, automatic localization is used for example in rotational angiography recordings. Besides this, a method of rendering visible is possible which is matched to other image recording methods which may have been used, for example, through markers being present on the electrodes which are visible in X-ray images and permit the most accurate possible positioning.

In an image data recording with X-rays, electrodes which are transparent to X-rays and/or electrodes with an X-ray absorbing marker can be used. The electrodes themselves and the manner in which they are attached must, however be chosen such that on the one hand they do not prevent use of the image data for diagnostic purposes or as part of further examinations, while at the same time, accurate localization has to be possible, for example through a marker. The use of specific markers can be particularly advantageous for carrying out automatic detection with the aid of a program means which is geared to the corresponding signal of the marker.

The model of conductivity and/or the spatial position of the electrodes and/or the equipotential surfaces and/or the point of intersection can be determined automatically or at least in part manually. It is thus possible to use a program means which, for example, automatically localizes the electrodes in the three-dimensional images, for which purpose appropriate algorithms for the image processing and analysis are optionally used. Likewise, the conductivity model can be determined automatically from the three-dimensional data, optionally in conjunction with additionally available data, via a program means. In addition, it is possible for manual inputs to be taken into account at least in part for the automatic determination, for example for adjusting the model in terms of special structural features in the body of the examination object, which special features the program means cannot per se take into account correctly. Advantageously, an essentially automatic processing, for example an automatic determination of the points of intersection of the equipotential surfaces is carried out, the result being presented to an operator who optionally can carry out corrections or can initiate a redetermination e.g. of the position of the electrodes using a different method.

The medical instrument can be displayed as per the determined spatial position with the recorded three-dimensional image data. In this way, the position of, for example, a catheter or a guide wire with a potential peak as an electrode can be displayed immediately in the recorded three-dimensional dataset, since the systems of coordinates of this dataset and of the catheter position match, so no time-consuming and error-prone image registration is required. Visualization can thus be carried out directly without any further conversion such as transformation of the coordinates, so, for example, the catheter position can be shown to the doctor or to a technician who is carrying out or monitoring an examination without any time delay.

Alternatively, the position of the instrument can also be displayed in other 3D image data which was previously combined with the dataset containing the electrodes using known methods of 3D/3D registration.

When more than three voltage values are determined at the electrode of the medical instrument, the spatial position can be determined by forming the average from the equipotential surfaces. Through averaging, a greater accuracy can optionally be achieved so an improved overall impression of the geometric conditions emerges. Errors in measurements of individual voltage values or in the conductivity model are offset by averaging where there is not a clear point of intersection.

In the case of instruments which contain multiple electrodes, the accuracy of the localization can be increased by additional consistency conditions.

In multi-electrode catheters for electrophysiology, the distance between the electrodes, for example, is approximately known. Here, the distances are fixed within defined limits by the rigidity of the catheter (maximum radius of curvature). These can influence the determination of position as additional constraints.

According to the invention, skin electrodes, in particular skin electrodes used for implementing electrophysiological methods, and/or electrodes inside the body, in particular electrodes of fixed-position medical instruments, can be used as electrodes. The electrodes can thus be placed deliberately onto the skin of the patient for estimating or determining the conductivity model, or electrodes are used which are in any case provided for other purposes such as monitoring or the like. In addition, fixed-position electrodes inside the body can be used, for example electrodes of fixed-position medical instruments or of implants. Since as a rule the number of electrodes inside the body is limited, combining these electrodes with further skin electrodes to form pairs is an obvious solution.

Advantageously, at least one or all the electrodes are arranged in the area of the image data recording. Consequently, the electrodes can be arranged for example in a typical field of view of 30 cm.

In the case of electrodes outside the imaging area, the intersecting planes in the three-dimensional image are determined manually or automatically, it being possible for the voltage drop missing outside the imaging area to be determined by a calibrating method. Optionally, information of other electrode pairs can also be used.

The use of special catheters is not necessary in the method according to the invention, but all electrophysiology catheters, for example, can be detected, as a result of which lower costs are incurred and, moreover, the locating of almost any number of catheters is possible.

A medical instrument comprising more than one electrode can be used for calibrating. Such a calibration offers the advantage that an absolute scaling of the voltage is obtained. For this purpose, a first electrode, then a second electrode are arranged, for example, in a front area of a catheter at a specified distance of, for example, 3 cm. In a non-flexible catheter, the distance is known so an absolute value of the voltage can thus be derived.

When the voltage is measured at the medical instrument, this may have to be based on an average in order to work out the spatial extension or to offset temporal fluctuations. To do this, measurements can optionally be made multiple times in succession or the extension of the catheter electrode or electrodes or the geometry of the instrument can be included in a calculation.

In addition, the invention relates to a device for localizing a medical instrument introduced into the body of an examination object, which device is fashioned for implementing the method outlined hereinabove. For this purpose, the device has means for generating and detecting signals in order to apply voltages or currents at electrodes and to record the corresponding signals. Furthermore, the device comprises an imaging medical examination device by means of which three-dimensional image data can be recorded. In order to determine a model of conductivity, a control device can access, as well as the image data, databases in which models of patient anatomy and further information are filed. Finally, the spatial position of the catheter or of a guide wire is determined via a program means of the control device as the point of intersection of equipotential surfaces.

BRIEF DESCRIPTION OF THE DRAWINGS

Further advantages, features and details of the invention will emerge from the exemplary embodiments below and from the drawings, in which.

DETAILED DESCRIPTION OF THE INVENTION

Figure 1:
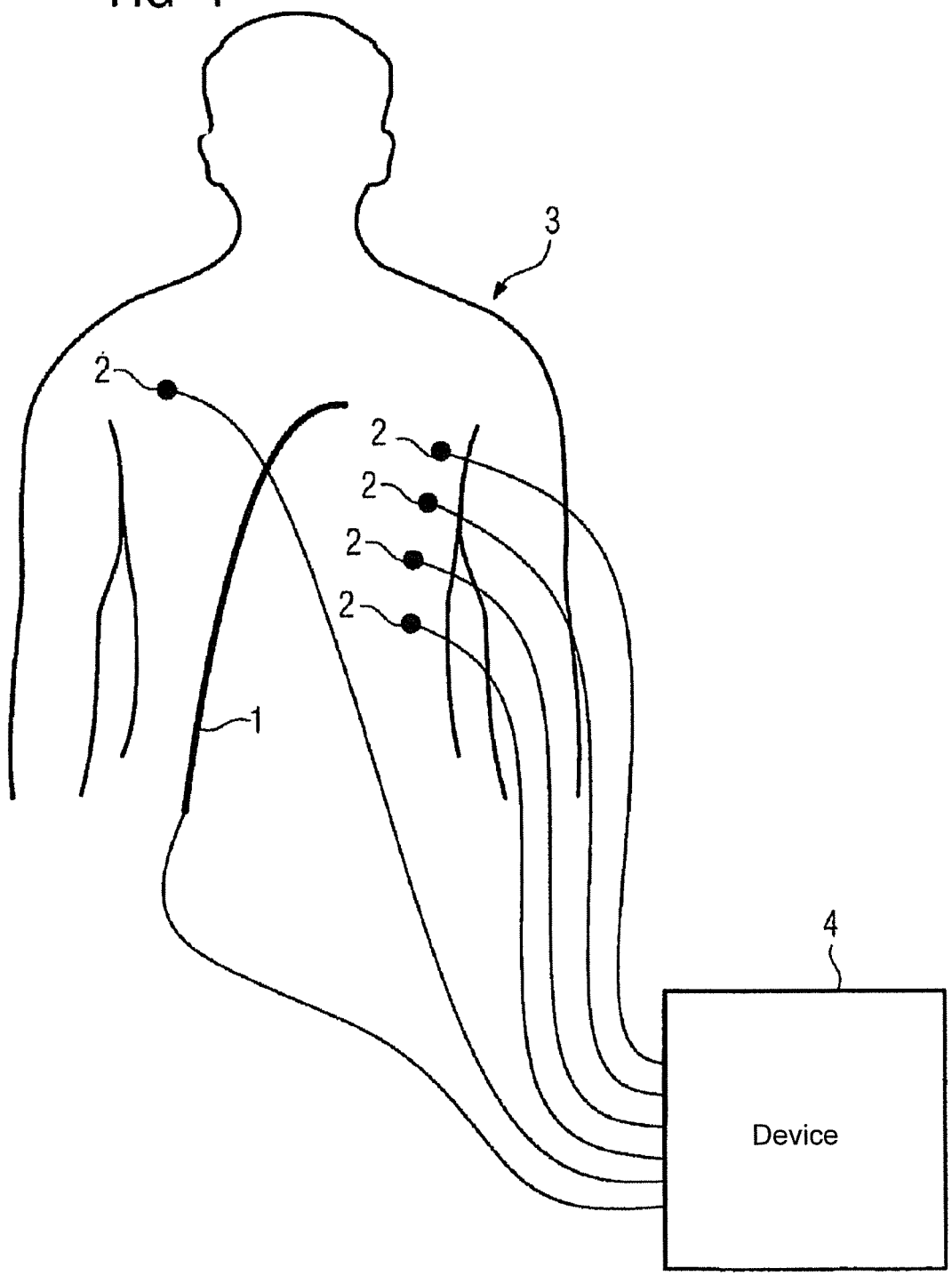
FIG. 1 shows a diagrammatic sketch of the arrangement of a catheter and of electrodes in a method according to the invention.

FIG. 1 shows a diagrammatic sketch of the arrangement of a catheter 1 and of electrodes 2 in a method according to the invention. The catheter 1 is introduced into the body of a patient 3 in order to be used there within the scope of an interventional procedure. Electrodes 2 are arranged on the patient 3, in this case five different skin electrodes. The electrodes 2 are arranged such that they do not all lie in one plane. The electrodes 2 and an electrode, not shown, of the catheter 1 are connected to a device 4 for generating and detecting signals, via which device voltages and/or currents can be applied and measured. In addition, by means of an imaging medical examination device, not shown here, for example for conducting a rotational angiography, three-dimensional image data of a region of interest of the body of the examination object is produced.

Figure 2:
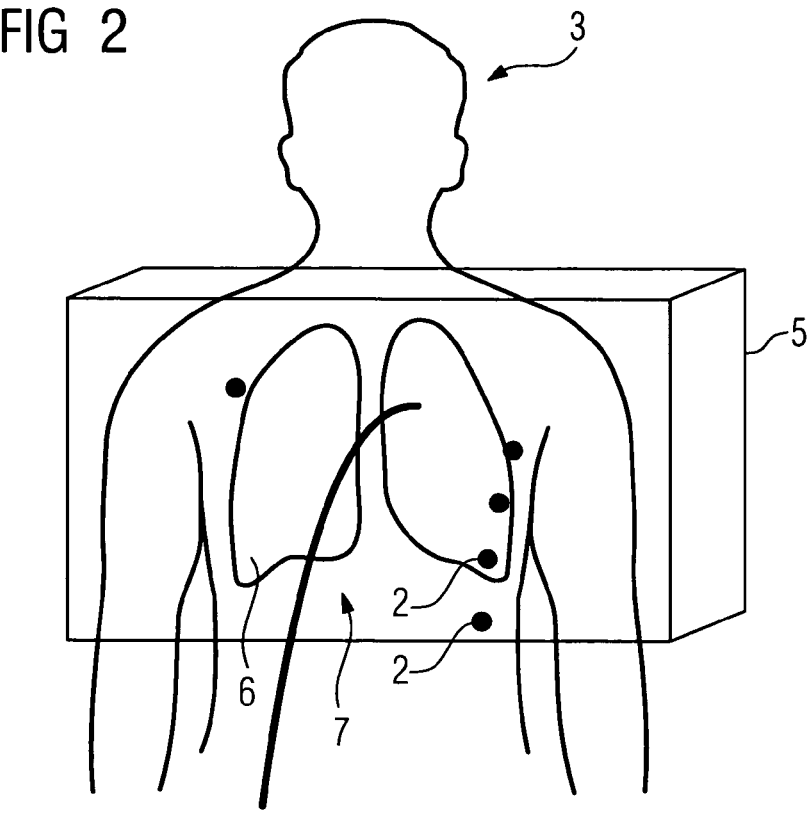
FIG. 2 shows a diagrammatic sketch of an image-recording volume comprising different tissue types.

FIG. 2 shows a sketch of an image-recording volume 5 of the patient 3 comprising different tissue types. Besides the five electrodes 2, lung tissue 6 is now shown which, in order to generate a conductivity model of the examination object, which here is a region of interest corresponding to the image-recording volume 5, is differentiated from other tissue 7. In order to obtain the conductivity model, the intensity values of the image data of the image-recording volume 5 are converted into conductivity values.

Figure 3:
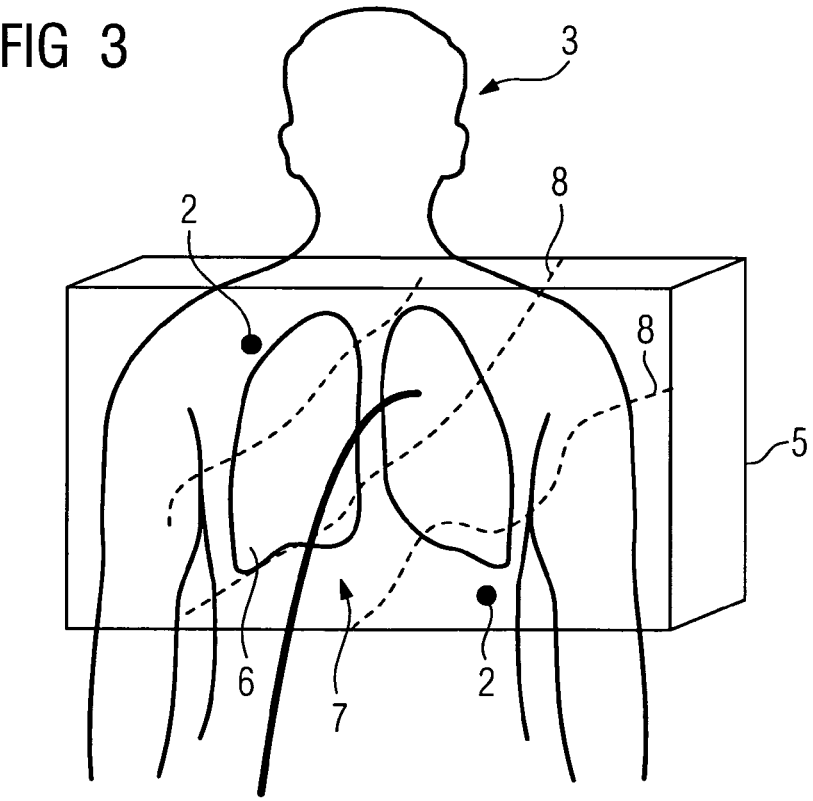
FIG. 3 shows a sketch concerning the localization of electrodes and the determination of electrical field distribution in a method according to the invention.

Finally, FIG. 3 shows how on the one hand the electrodes 2 are localized and on the other the electrical field distribution is determined in the image-recording volume 5. The electrodes 2, of which only a pair are shown here, are localized in the three-dimensional images of the image-recording volume 5 automatically via a corresponding program means when a rotational angiography is carried out. In relation to the electrodes 2 of the pair shown here, the path of the electric field distribution is determined for an e.g. constant voltage or an e.g. constant current with the aid of the conductivity model and of the electrode positions which are now known. In this process, equipotential surfaces 8, i.e. areas with in this case a constant voltage, emerge, which define the field distribution for a predetermined value of the electrode voltage. Alternatively, an alternating voltage or an alternating current with a constant mean value over a certain time period can also be operated with. The use of constant voltage/constant current is described below, however, by way of example.

Figure 4:
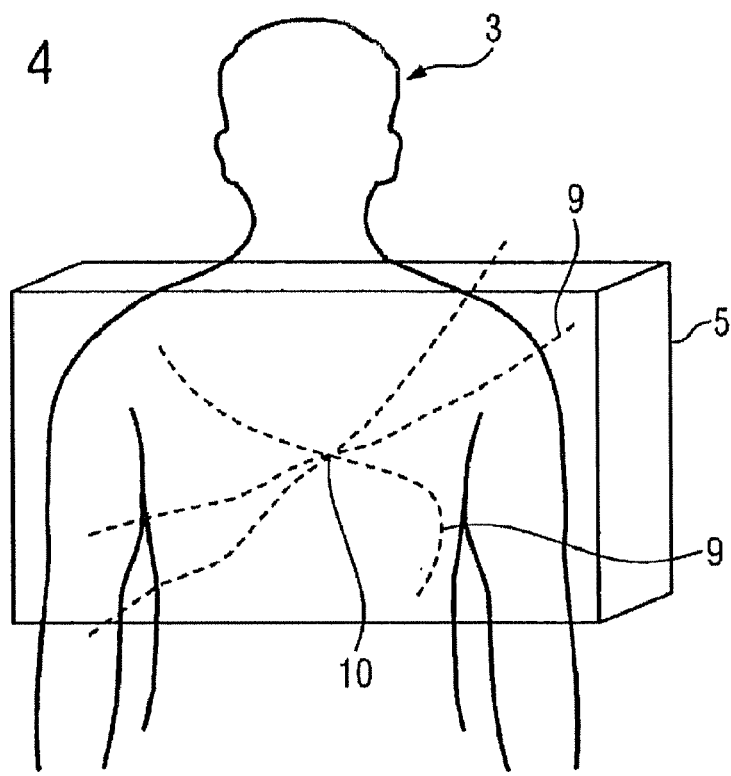
FIG. 4 shows a sketch concerning the determination of the catheter position in a method according to the invention and FIG. 5 shows a device according to the invention for the localization of a medical instrument introduced into the body of an examination object.

FIG. 4 shows a sketch concerning the determination of the catheter position in a method according to the invention, the patient 3 and the image-recording volume 5 again being shown. The electrode positions are not reproduced here for reasons of clarity. As shown in FIG. 4, a fixed voltage or a fixed current is applied at each of the two electrodes, whereupon the voltage at an electrode of the catheter 1 is measured. To do this, a voltage or a current with a predetermined value is now actually applied, and the mean value of the catheter electrode recorded. From the known equipotential surfaces for the voltage value being applied, which equipotential surfaces were determined as an electric field distribution from the conductivity model and the electrode positions, equipotential surfaces 9 are determined for each of three electrode pairs, which equipotential surfaces are a selection of the equipotential surfaces 8 which are in each case associated with the measured value of the catheter electrode. Since the electrode pairs were selected such that not all the electrodes 2 lie in a plane, a clear intersection 10 emerges which corresponds to the spatial position of the catheter 1.

The catheter position can be represented directly without a separate registration with the three-dimensional image dataset of the image-recording volume 5. The display can be made here such that only the catheter tip or an electrode position which corresponds to the point of intersection 10 is shown or such that the complete medical instrument, i.e. the catheter 1 is at least approximately reconstructed or sketched for the display. If an instrument possesses multiple electrodes, these can be localized and shown individually.

In this way, it is possible by means of the method according to the invention to obtain a high level of geometric accuracy in the localization of a medical instrument in the body of an examination object. Thus, in particular critical examinations for example of the heart can be carried out with a high degree of accuracy to within a range of one millimeter.

Figure 5:
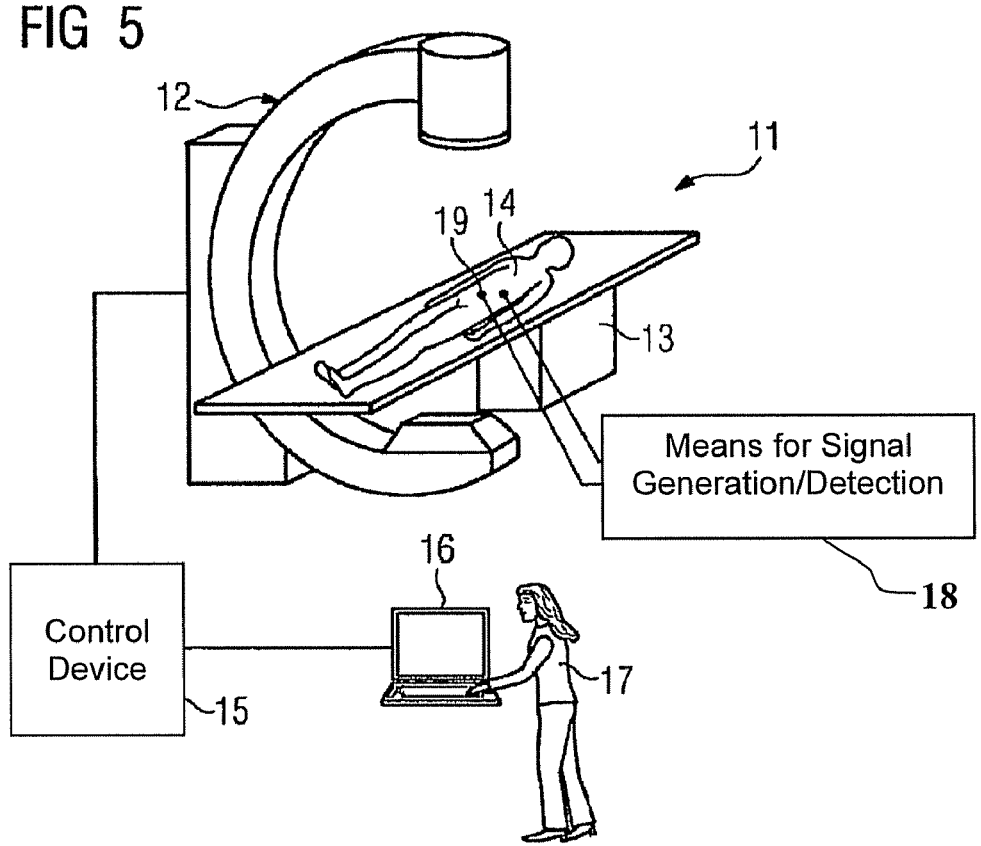

FIG. 5 shows a device 11 according to the invention for localizing a medical instrument introduced into the body of an examination object. The device 11 has a C-arm system 12 for performing a rotational angiography on a patient 14 located on a patient table 13. The C-arm system 12 for performing the rotational angiography is controlled via a control device 15 to which an image output means 16 with an input device is connected, which an operator 17 can use for inputs or for initiating a recording or the like. Furthermore, the device 11 comprises means for signal generation and detection which are labeled with the reference character 18. These means 18 are connected to electrodes 19 which are arranged as skin electrodes on the body of the patient 14. For reasons of clarity, further skin electrodes and their connection to the means 18 are not shown. In addition, there is a connection from the means 18 for signal generation and detection to an electrode, not shown here, of a medical instrument introduced into the body of the patient 14.

With the aid of the C-arm system 12 of the device 11, three-dimensional image data is generated of a body region of interest of the examination object, i.e. of the patient 14, corresponding here to the area on which the electrodes 19 are located of the upper body. From this, a model of the electric conductivity of the patient 14 is derived with the aid of the control device 15 on which corresponding program means are available. In addition, electric field distributions which would be produced if a constant voltage or a constant current were applied are determined as a function of this conductivity model and the spatial positions of the electrodes 19. The equipotential surfaces are thus derived from the conductivity model and the electrode positions.

Then, constant voltages or constant currents, for example, are applied here also at each pair of electrodes 19, and the voltage at the electrode of the mechanical instrument is recorded. Such a determination of voltage values for an actually applied voltage or applied current is performed for at least three electrode pairs, equipotential surfaces being obtained in relation to the voltage values on the medical instrument, which equipotential surfaces intersect at a point. If more than three equipotential surfaces are determined, as values for more than three electrode pairs are recorded, then the position of the medical instrument is determined by averaging. The known position of the medical instrument can be shown with the aid of the control device 15 on image output means 16 together with the three-dimensional image data which were recorded with the C-arm system 12.

Here, the device 11 exhibits a high positioning accuracy for localizing the medical instrument, without special catheters having to be used.

The invention claimed is:

1. A method for locating a medical instrument introduced into a body of an examination object, comprising:
   arranging at least four electrodes at the body of the examination object;
   recording a three-dimensional image data of a body region of the examination object by an imaging medical examination device;
   determining an electrical conductivity model of the examination object as a function of the three-dimensional image data;
   determining an electric field distribution, including a respective location of a plurality of equipotential surfaces having a constant voltage, of the examination object as a function of the electrical conductivity model and spatial positions of the electrodes based on a voltage being applied for at least three different electrode pairs formed from the four electrodes which do not all lay in one plane;
   applying the voltage at each of the three electrode pairs respectively;
   determining three voltage values at an electrode of the medical instrument for the applied voltage at each of the three electrode pairs respectively;
   determining a spatial position of the medical instrument as a point of an intersection of the equipotential surfaces assigned to the three voltage values at the electrode of the medical instrument;
   and wherein more than three voltage values are determined at the electrode of the medical instrument, the spatial position of the medical instrument is determined by averaging the voltage values from the equipotential surfaces.

2. The method as claimed in claim 1, wherein the electrical conductivity model is determined as a function of an assignment of an intensity value of the image data to a conductivity value.

3. The method as claimed in claim 1, wherein at least two different tissue types with differing conductivities are differentiated in the body of the examination object for determining the electrical conductivity model.

4. The method as claimed in claim 3, wherein the different tissue types are selected from the group consisting of: bone tissue, organ tissue, air-equivalent tissue, and water-equivalent tissue.

5. The method as claimed in claim 1, wherein the three-dimensional image data is recorded by a method selected from a group consisting of: a rotational angiography, a computer tomography, a magnetic resonance recording, and an ultrasound recording.

6. The method as claimed in claim 1, wherein different image recording methods are combined for recording the three-dimensional image data or for determining the spatial positions of the electrodes.

7. The method as claimed in claim 1, wherein the spatial positions of the electrodes are determined from the three-dimensional image data.

8. The method as claimed in claim 7, wherein X-ray transparent electrodes or electrodes with an X-ray absorbing marker are used when the image data is recorded using X-rays.

9. The method as claimed in claim 1, wherein the medical instrument and the spatial position of the medical instrument are displayed at a display unit.

10. The method as claimed in claim 1, wherein the electrodes comprise skin electrodes and inside of the body electrodes.

11. The method as claimed in claim 10, wherein the skin electrodes are electrodes implementing an electrophysiological method and the inside of the body electrodes are electrodes of a fixed-position medical instrument inside of the body.

12. The method as claimed in claim 11, wherein the electrode pair is formed from one of the skin electrodes and one of the inside of the body electrodes.

13. The method as claimed in claim 1, wherein at least one of the electrodes is arranged in an area of the image data recording.

14. The method as claimed in claim 1, wherein at least one of the electrodes is arranged outside an area of the image data recording and a voltage drop outside the area of the image data recording is determined by a calibrating method or by information of at least one other electrode pair.

15. The method as claimed in claim 14, wherein a medical instrument comprising more than one electrode is used for calibrating.

16. A method for locating a medical instrument introduced into a body of an examination object, comprising:
   arranging at least four electrodes at the body of the examination object;
   recording a three-dimensional image data of a body region of the examination object by an imaging medical examination device;
   determining an electrical conductivity model of the examination object as a function of the three-dimensional image data;
   determining an electric field distribution, including a respective location of a plurality of equipotential surfaces having a constant voltage, of the examination object as a function of the electrical conductivity model and spatial positions of the electrodes based on a current being applied for at least three different electrode pairs formed from the four electrodes which do not all lay in one plane;
   applying the current at each of the three electrode pairs respectively;
   determining three voltage values at an electrode of the medical instrument for the applied current at each of the three electrode pairs respectively;
   determining a spatial position of the medical instrument as a point of an intersection of the equipotential surfaces assigned to the three voltage values at the electrode of the medical instrument; and
   wherein more than three voltage values are determined at the electrode of the medical instrument, the spatial position of the medical instrument is determined by averaging the voltage values from the equipotential surfaces.

17. A device for locating a medical instrument introduced into a body of a patient, comprising:
   a patient supporting table which supports a patient having at least four electrodes arranged at the body of the patient;
   a unit connected with the electrodes which generates and detects signals of the electrodes;
   a medical imaging device which records a three-dimensional image data of a body region of the patient; and
   a processing device which:
      determines an electrical conductivity model of the patient as a function of the three-dimensional image data, determines an electric field distribution, including a respective location of a plurality of equipotential surfaces having a constant voltage, of the patient as a function of the electrical conductivity model and spatial positions of the electrodes based on a voltage being applied for at least three different electrode pairs formed from the four electrodes which do not all lay in one plane, determines three voltage values at an electrode of the medical instrument after applying the voltage at each of the three electrode pairs respectively, determines a spatial position of the medical instrument as a point of an intersection of the equipotential surfaces assigned to the three voltage values at the electrode of the medical instrument; and wherein more than three voltage values are determined at the electrode of the medical instrument, the spatial position of the medical instrument is determined by averaging the voltage values from the equipotential surfaces.

* * * * *